United States Patent [19]

Goldstein

[11] 4,010,148
[45] Mar. 1, 1977

[54] PURIFIED THYMOSIN AND PROCESS

[75] Inventor: Allan Leonard Goldstein, Galveston, Tex.

[73] Assignee: Board of Regents of the University of Texas System, Galveston, Tex.

[22] Filed: May 12, 1975

[21] Appl. No.: 576,509

[52] U.S. Cl. .............................. 260/112 R; 424/177; 260/112.5 R
[51] Int. Cl.$^2$ .................. C07C 103/52; C07G 7/00
[58] Field of Search ................ 260/112.5 R, 112 R; 424/177

[56] References Cited
FOREIGN PATENTS OR APPLICATIONS 7,373  10/1969  France

OTHER PUBLICATIONS

Goldstein et al.: Chem. Abstr. 74:28457f (1971).
White et al.: Chem. Abstr. 75:72007d (1971).
White et al.: Chem. Abstr. 75:59235g (1971).

*Primary Examiner*—Lewis Gotts
*Assistant Examiner*—Reginald J. Suyat
*Attorney, Agent, or Firm*—Samuel L. Welt; George M. Gould

[57] ABSTRACT

A highly purified extract of the mammalian thymus gland and a process for its preparation is described. This extract is a hormonally active proteinaceous material which is involved in the regulation of cell-mediated immunity. The hormone has been named thymosin.

9 Claims, No Drawings

PURIFIED THYMOSIN AND PROCESS

BACKGROUND OF THE INVENTION

The partial purification of the thymic hormone thymosin has been described by Goldstein et al., Proc. Nat. Acad. Sci. (U.S.A.) 56, 1010–1017 (1966).

An even cruder form of thymosin and a method for its preparation is described in French Medicinal Pat. No. 7,373 delivered Oct. 27, 1969, which claims priority from U.S. Pat. Application Ser. No. 580,558, filed Aug. 24, 1966, inventors Abraham White and Allan L. Goldstein, now abandoned.

Thymosin fraction 5 which has been widely employed recently in the biological investigations of thymosin is known to contain at least 12 heat-stable acidic peptides and proteins with molecular weights that range from 1,200 to 14,000.

More recently Goldstein et al., Proc. Nat. Acad. Sci. (U.S.A.) 69, 1800–1803 (1972) described an improved purification procedure for thymosin. It is believed that the material obtained by this process which is indicated to be homogeneous, in fact comprises at least three separate components when examined electrophoretically on 15% polyacrylamide gel.

Thus thymosin materials previously available in the art have all been non-homogeneous preparations and therefore not suited for use in chemical structure elucidation studies which are necessary before chemical approaches leading to the synthetic preparation of this biologically valuable hormone can be achieved. In addition homogeneous thymosin preparations are valuable as starting materials in preparing highly specific antibodies to thymosin which in turn are the basis for sensitive and efficient immunoassays for this hormone.

DESCRIPTION OF THE INVENTION

The present invention relates to a novel thymosin extract which has been purified to homogeneity. This extract, identified as thymosin fraction 8, is seen to migrate during electrophoresis as a single band on 15% polyacrylamide gels at pH 8.3 and 2.9. Fraction 8 is essentially free of carbohydrate, lipid and nucleotide and contains no cyclic AMP.

Amino acid analysis of this homogeneous thymosin fraction derived from bovine thymus glands indicates that this material is a protein containing 108 amino acid residues and has a molecular weight of approximately 12,200. The amino acid analysis of thymosin fraction 8 is set forth in the following table:

TABLE 1

AMINO ACID COMPOSITION OF BOVINE THYMOSIN FRACTION 8

| Amino acid | Residues/molecule | Amino acid | Residues/molecule |
|---|---|---|---|
| Lysine | 4 | Alanine | 7 |
| Histidine | 1 | Cysteine[b] | 1 |
| Arginine | 2 | Valine | 5 |
| Aspartic acid | 22 | Methionine[b] | 2 |
| Thronine[a] | 4 | Isoleucine | 3 |
| Serine[a] | 5 | Leucine | 6 |
| Glutamic acid | 32 | Tyrosine | 1 |
| Proline | 5 | Phenylalanine | 2 |
| Glycine | 6 | Total | 108 |

The data are presented as assumed numbers of residues per molecule.
The molecular weight is approximately 12,200. A separate analysis for tryptophan was performed.
[a]Extrapolated to zero time from 24, 48 and 72 hour hydrolysates.
[b]Determine as cysteic acid and methionine sulfone by performic acid oxidation.

The purification of thymosin fraction 8 is conveniently carried out according to the following process. Thymus tissue derived from a suitable mammalian source, such as bovine, calf, human, rat, mouse or the like thymus glands and quick frozen for storage, is thawed and trimmed free of adipose tissue. It is generally desirable to utilize up to about 5 kg. of tissue per batch and the instant description will relate to a 5 kg. batch.

It is to be noted that standard precautions against bacterial contamination should be taken throughout and the preparation should be routinely checked for pyrogenicity by both the limulus endotoxin assay (Cooper et al., J. Lab. Clin. Med. 78, 138–137 (1973) and the rabbit pyrogenicity assay (McClosky et al., (1971)). Pyrogen free sterile water is employed throughout and all procedures are performed at 4° C. unless stated otherwise.

The aforesaid trimmed thymus tissue is homogenized in three volumes of dilute aqueous saline solution such as 0.15 M NaCl containing an anti-foaming agent such as 1% octyl alcohol (v/v) in a suitable blender for from 2 to 3 minutes, preferably 3 minutes at top speed.

The resulting homogenate is then centrifuged at from 12,000 to 14,000 xg., preferably at about 14,000 xg. to sediment the nuclear material. Two liter portions of the supernatant are then heated with stirring to 80° C. in a boiling water bath.

The voluminous precipitate of heat-denatured protein is removed by filtration. After cooling to 4° C., the clear yellow filtrate is added slowly, with stirring, to 5 volumes of acetone at a temperature of −20° to −5° C., preferably at about −10° C. The precipitate is collected on a large Buchner funnel, washed with several volumes of cold (−10° C.) acetone, and dried in a dessicator under reduced pressure.

The resulting white powder is suspended in about 10 volumes of 10mM NaPO$_4$, pH 7.0 and stirred at room temperature for from 30 min. to 1½ hours, preferably one hour. A small amount of insoluble residue is removed by centrifugation at from 12,000 to 15,000 xg. preferably at about 15,000 xg. and the sample is adjusted to a protein concentration of 25 mg/ml. as determined by the Lowry procedure (Lowry et al., J. Biol. Chem. 193, 265–275 (1951)).

Saturated ammonium sulfate solution is adjusted to pH 7.0 with ammonium hydroxide is added (33.3 ml. to each 100 ml. of solution), and the solution is stirred for 45 min. to 1 hour, preferably one hour. After centrifugation at from 5,000 to 15,000 xg., preferably 15,000 xg. to remove precipitated material, the supernatant is adjusted to pH 4.0 with 10% acetic acid. Solid ammonium sulfate (14.6 g/100 ml.) is added and the suspension is stirred for 45 min. to 1 hour, preferably one hour.

The resulting precipitate is collected by centrifugation at from 5,000 to 15,000 xg., preferably 15,500 xg., and is dissolved in about 10 nM of Tris HCl pH 8.0 at a concentration of from 8 to 12 mg/ml. protein, preferably 10 mg/ml. protein. The solution is subjected to ultrafiltration at room temperature in a hollow fiber system preferably an Amicon DC-2-system-concentration mode, H1DP10 membrane cartridge. Such ultrafiltration serves to remove materials having a molecular weight of 15,000 and greater.

The filtrate from the ultrafiltration is collected at 4° C., concentrated by rotary evaporation under reduced pressure and desalted on a 5 × 80 cm. column of Sephadex G-25 (fine) equilibrated with dionized water. The protein peak which elutes in advance of the salt and nucleotide peak is pooled, concentrated by rotary evaporation, and dried by lyophilization.

One gram of the lyophilized protein is then dissolved in 100 ml. of 50 mM Tris-Cl, 10 mM mercaptoethanol, pH 8.0 and the resulting solution is percolated through a 2 × 40 cm column of DEAE cellulose (Whatman DE-32) equilibrated with the same buffer. After washing the column with one bed volume of starting buffer, the chromatogram is developed with a linear gradient formed by 800 ml. of 10 mM mercaptoethanol in 50 mM Tris-Cl, pH 8.0, as the starting buffer and 800 ml. of 10 mM mercaptoethanol, 0.8 M NaCl in 50 mM Tris-Cl, pH 8.0 as the limit buffer.

The thymosin containing fractions, as determined by bioassay such as described in Bach et al., Proc. Nat. Acad. Sci. (U.S.A.) 68, 2734–2738 (1971), and Cohen et al., Ann. N.Y. Acad. Sci., Vol. 249, 145–153 (1975) are pooled and subjected to gel filtration on a 3.8 × 150 cm column of Sephadex G-50 (fine) equilibrated with 0.2 M KCl and 10 mM mercaptoethanol in 10 mM-Tris-Cl, pH 8.0.

The active fractions as determined by bioassay, are desalted by gel filtration on Sephadex G-25 and then subjected to preparative polyacrylamide gel electrophoresis. This procedure utilizes a 15% acrylamide gel (6 cm high) that has been electrophoresed with 5 mmoles of cysteine as a free radical scavenger. The sample (150–200 mg.) is electrophoresed at 100 milli-amps using a standard pH 8.3 Tris-glycine buffer system. The first protein peak eluted from the gel is thymosin fraction 8.

Comparison of the above process with previously known procedures for purifying thymosin indicates that the steps beyond the ammonium sulfate precipitation in the instant process are novel and thus represent the process aspect of the present invention. A particular preferred aspect of said process is the improved preparation of thymosin fraction 5.

For the purpose of convenience the various intermediate thymosin extract products are given fraction number designations as follows:

| | |
|---|---|
| 14,000 xg. Centrifugation product | - Fraction 1 |
| 80° C. heat step filtrate | - Fraction 2 |
| Acetone precipitate | - Fraction 3 |
| Ammonium sulfate precipitate | - Fraction 4 |
| Ultrafiltration + Sephadex G-25 desalted peak | - Fraction 5 |
| DEAE Cellulose peaks | - Fraction 6 |
| Sephadex G-50 peaks | - Fraction 7 |
| Polyacrylamide Gel Electrophoresis product peak | - Fraction 8 |

I claim:

1. In a process for recovering a biologically active protein component from thymus tissue, said process comprising
   i. homogenizing and extracting thymic tissue in aqueous saline solution, then centrifuging to remove undissolved material;
   ii. heat treating the centrifuge supernatant at about 80° C., which treatment precipitates undesired fraction then centrifuging to remove the precipitated portions;
   iii. admixing the supernatant with a large excess of cold acetone, thereby precipitating the active fraction, and collecting said precipitate;
   iv. dissolving the acetone precipitate in phosphate buffer, then adding ammonium sulfate to about 25% of saturation and removing non-soluble impurity; and
   v. increasing the ammonium sulfate content to about 50% of saturation, thereby precipitating the active fraction; the improvement which comprises in combination
   A. dissolving the collected precipitate from step (v) in phosphate buffer and ultrafiltering the solution using a membrane having a molecular weight cut-off of 15,000;
   B. concentrating the ultrafiltration filtrate and treating the residue by column chromatography to thereby separate salt and nucleotides;
   C. isolating the protein peak from (B) and then additionally purifying the protein material by column chromatography followed by gel filtration and then gel electrophoresis.

2. The process of claim 1 wherein said ultrafiltration is conducted in a hollow fiber system.

3. The process of claim 1 wherein the column chromatography of step (B) is conducted on Sephadex G-25.

4. The process of claim 1 wherein the gel filtration of step (C) is conducted on Sephadex G-50.

5. The process of claim 1 wherein the gel electrophoresis is conducted on 15% polyacrylamide gel using pH 8.3 buffer.

6. The process of claim 1 wherein bovine thymus tissue is employed and the protein component isolated is essentially free of carbohydrate, lipid, nucleotide and cyclic AMP, is homogeneous on 15% polyacrylamide gel electrophoresis at pH 8.3 and 2.9, has a molecular weight of about 12,200 and an amino acid composition as follows:

| Amino acid | Residues/molecules |
|---|---|
| Lysine | 4 |
| Histidine | 1 |
| Arginine | 2 |
| Aspartic acid | 22 |
| Threonine | 4 |
| Serine | 5 |
| Glutamic acid | 32 |
| Proline | 5 |
| Glycine | 6 |
| Alanine | 7 |
| Cysteine | 1 |
| Valine | 5 |
| Methionine | 2 |
| Isoleucine | 3 |
| Leucine | 6 |
| Tyrosine | 1 |
| Phenylalanine | 2 |
| Total | 108 |

7. An improved process for preparing thymosin fraction 5 which process comprises ultrafiltering a solution of thymosin fraction 4 in phosphate buffer using a membrane having a molecular weight cut-off of 15,000 concentrating the ultrafiltration filtrate and treating the residue by column chromatography to thereby separate salt and nucleotide.

8. The process of claim 7 wherein said ultrafiltration is conducted in a hollow fiber system.

9. The process of claim 7 wherein said column chromatography is conducted on Sephdex G-25.

* * * * *

UNITED STATES PATENT AND TRADEMARK OFFICE
CERTIFICATE OF CORRECTION

PATENT NO. : 4,010,148

DATED : March 1, 1977

INVENTOR(S) : Allan Leonard Goldstein

It is certified that error appears in the above-identified patent and that said Letters Patent are hereby corrected as shown below:

In the abstract, add the following paragraph:

The invention described herein was made in the course of work under a grant or award from the Department of Health, Education and Welfare.

Signed and Sealed this

Fourth Day of October 1977

[SEAL]

Attest:

RUTH C. MASON
Attesting Officer

LUTRELLE F. PARKER
Acting Commissioner of Patents and Trademarks